(12) United States Patent
McCalmont et al.

(10) Patent No.: US 11,484,216 B2
(45) Date of Patent: Nov. 1, 2022

(54) MODULAR WEARABLE SENSOR

(71) Applicant: BraveHeart Wireless Inc., Nashua, NH (US)

(72) Inventors: Stephen A McCalmont, Hollis, NH (US); Stuart P. MacEachern, Hopkinton, MA (US); Sharon Lake, Longmont, CO (US)

(73) Assignee: BraveHeart Wireless Inc., Nashua, NH (US)

( * ) Notice: Subject to any disclaimer, the term of this patent is extended or adjusted under 35 U.S.C. 154(b) by 0 days.

(21) Appl. No.: 17/218,654

(22) Filed: Mar. 31, 2021

(65) Prior Publication Data

US 2021/0212578 A1   Jul. 15, 2021

Related U.S. Application Data

(63) Continuation-in-part of application No. 16/591,882, filed on Oct. 3, 2019.

(60) Provisional application No. 62/807,348, filed on Feb. 19, 2019.

(51) Int. Cl.

| | |
|---|---|
| *A61B 5/026* | (2006.01) |
| *A61B 5/24* | (2021.01) |
| *A61B 5/1455* | (2006.01) |
| *G06F 1/16* | (2006.01) |

(52) U.S. Cl.
CPC ........ *A61B 5/0261* (2013.01); *A61B 5/14552* (2013.01); *A61B 5/24* (2021.01); *G06F 1/163* (2013.01)

(58) Field of Classification Search
CPC ..... A61B 5/0261; A61B 5/14552; A61B 5/24; A61B 5/6833; G06F 1/163; G06F 3/011; G06F 3/015
See application file for complete search history.

(56) References Cited

U.S. PATENT DOCUMENTS

| | | | |
|---|---|---|---|
| 10,835,106 B1 * | 11/2020 | Ubbesen | G06F 1/1656 |
| 2008/0287748 A1 | 11/2008 | Sapounas et al. | |
| 2009/0088614 A1 | 4/2009 | Taub | |
| 2013/0060098 A1 * | 3/2013 | Thomsen | A61B 5/14551 600/301 |

(Continued)

FOREIGN PATENT DOCUMENTS

WO    WO-9959465 A1 * 11/1999 ........... A61B 5/0002

OTHER PUBLICATIONS

Office Action for U.S. Appl. No. 16/591,882, dated Apr. 12, 2021, 13 Pages.

(Continued)

*Primary Examiner* — Brian T Gedeon
*Assistant Examiner* — Joshua Andrew Schum-Houck
(74) *Attorney, Agent, or Firm* — Maine Cernota & Rardin

(57) ABSTRACT

A modular wearable health monitor having a substantially flexible attachment means connected to a housing comprising a power source and at least one processor through a relatively rigid and narrow spine disposed substantially centrally thereon having a variety of clinical and non-clinical uses that provides more comfortable and durable attachment of biometric sensors to a user by allowing the attachment means to contour to the user's body without the housing also being forced to do so along its entire width.

20 Claims, 5 Drawing Sheets

(56) References Cited

U.S. PATENT DOCUMENTS

| | | | |
|---|---|---|---|
| 2015/0305974 A1* | 10/2015 | Ehrenreich | A61H 23/0236 |
| | | | 601/46 |
| 2015/0351690 A1 | 12/2015 | Toth et al. | |
| 2016/0120434 A1* | 5/2016 | Park | G16H 50/30 |
| | | | 600/301 |
| 2016/0263395 A1 | 9/2016 | Siegel et al. | |
| 2016/0266606 A1* | 9/2016 | Ricci | H04M 1/72412 |
| 2018/0209814 A1 | 7/2018 | Yamada et al. | |

OTHER PUBLICATIONS

Office Action for U.S. Appl. No. 16/591,882, dated Aug. 2, 2021, 16 Pages.
Final Office Action for U.S. Appl. No. 16/591,882 dated Mar. 16, 2022, 26 pages.
Office Action for U.S. Appl. No. 16/591,882 dated Nov. 23, 2021, 18 Pages.

* cited by examiner

MODULAR WEARABLE SENSOR

RELATED APPLICATIONS

This application is a Continuation In Part of U.S. application Ser. No. 16/591,882, filed Oct. 3, 2019, which claims the benefit of U.S. Provisional Patent No. 62/807,348, filed Feb. 19, 2019. These applications are herein incorporated by reference in their entirety, for all purposes.

FIELD OF THE INVENTION

The invention relates to medical sensors and, more particularly, to modular, fully-featured wearable medical sensors suitable for use in clinical and non-clinical environments.

BACKGROUND OF THE INVENTION

The wearable medical device market has expanded greatly over the past decade, with consumer devices, such as the Fitbit® and Jawbone® wireless activity trackers, becoming a popular way for people to quantify and take charge of their personal fitness and overall well-being. While these devices are the most visible to consumers, rapid developments are simultaneously occurring in similar devices having a wide range of clinical uses. These devices are constantly becoming smaller, offering better battery life through both new battery chemistries and more efficient electronics, while providing more data and using better and more efficient algorithms to render that data useful. Existing clinical and other full-featured devices, however, are still relatively bulky and, as a consequence, uncomfortable to wear.

Although some clinical devices can be worn as a wristwatch, dependent on the biometric function(s) desired to be monitored, positioning of a wearable sensor, or even multiple wearable sensors, in various, specific locations on the body may be required to monitor certain biometric functions. Depending on the form factor and placement of the wearable sensor, clothing items and accessories may become wedged between the device and the body of a user thereof. At best, this causes only user discomfort while, at worst, this can interfere with the monitoring capabilities of the wearable sensor and result in inaccuracies.

Placement of wearable sensors on locations other than a user's wrist is currently accomplished through the use of temporary adhesives, similar to those used in bandages. The form factor of such devices is generally similar to a medium-sized bandage.

The sensors and associated circuitry of such devices are typically either secured to the bandage-like adhesive or contained within it. As the circuit boards and other electronic components of prior art devices are at least semi-rigid, this results in the device, during use, exerting continuous outward (i.e. away from the user) pressure on the adhesive when affixed to a curved portion of the user's body. This results in an uncomfortable pulling sensation on the user while also causing the sensor to tend to detach therefrom. This tendency is exacerbated by the user's movements, which result in spikes of outward pressure due to movement-related, minor changes in the curvature of the portion of the user's body onto which the device is affixed.

As the adhesive, being a temporary adhesive, weakens over time, these forces ultimately cause the adhesive to fail, often prior to the time at which the sensor was intended to be removed. Such a failure results in data loss, in addition to a reduction in the cost/benefit ratio of the devices generally. In many cases, this failure also requires a new sensor to be placed on the user, which may require the user to visit a medical facility, at the very least resulting in a significant inconvenience. In some cases, such a failure may even trigger a false alarm, potentially diverting medical resources from a true emergency.

The use of stronger adhesives would potentially resolve issues relating to the adhesive failing early, but would likely also result in additional discomfort to the user upon sensor removal and would not relieve the general discomfort associated with the use of such sensors.

The use of flexible circuit boards would also tend to ameliorate some of these issues, but would also increase the cost of such devices and potentially limit which sensors could be installed thereon.

Furthermore, in some cases, a disposable wearable sensor that resolves the aforementioned issues with the prior art, while being configured to discourage reuse, is needed.

What is needed, therefore, are wearable health monitors that can be secured to any location on a human body that may be needed for monitoring a biometric function or functions, that is able to better adhere to a user for the desired duration of monitoring while maintaining or increasing monitoring capabilities over the prior art and increasing user comfort, and that can be configured for reuse or one-time use while maintaining the aforementioned benefits.

SUMMARY OF THE INVENTION

An objective of embodiments of the present disclosure is to provide a wearable health monitor that is modular, allowing for the majority of circuitry to be separated from the adhesive portion thereof, which, in embodiments, is disposable.

A further objective of embodiments of the present disclosure is to reduce the amount of circuitry disposed on the adhesive portion of the wearable health monitor described herein, allowing the wearable health monitor to better contour to a user's body.

Still another object of embodiments of the present invention is to provide a wearable health monitor of improved durability and reusability.

Still even another object of embodiments of the present invention is to improve the ease of use of wearable health monitors, generally.

Still even yet another object of embodiments of the present invention is to achieve the aforementioned objectives using a disposable wearable health monitor.

Still even a yet further object of embodiments of the present invention is to prevent clothing items and accessories from becoming wedged between the wearable health monitor and the body of a user thereof.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION

Figure 1:
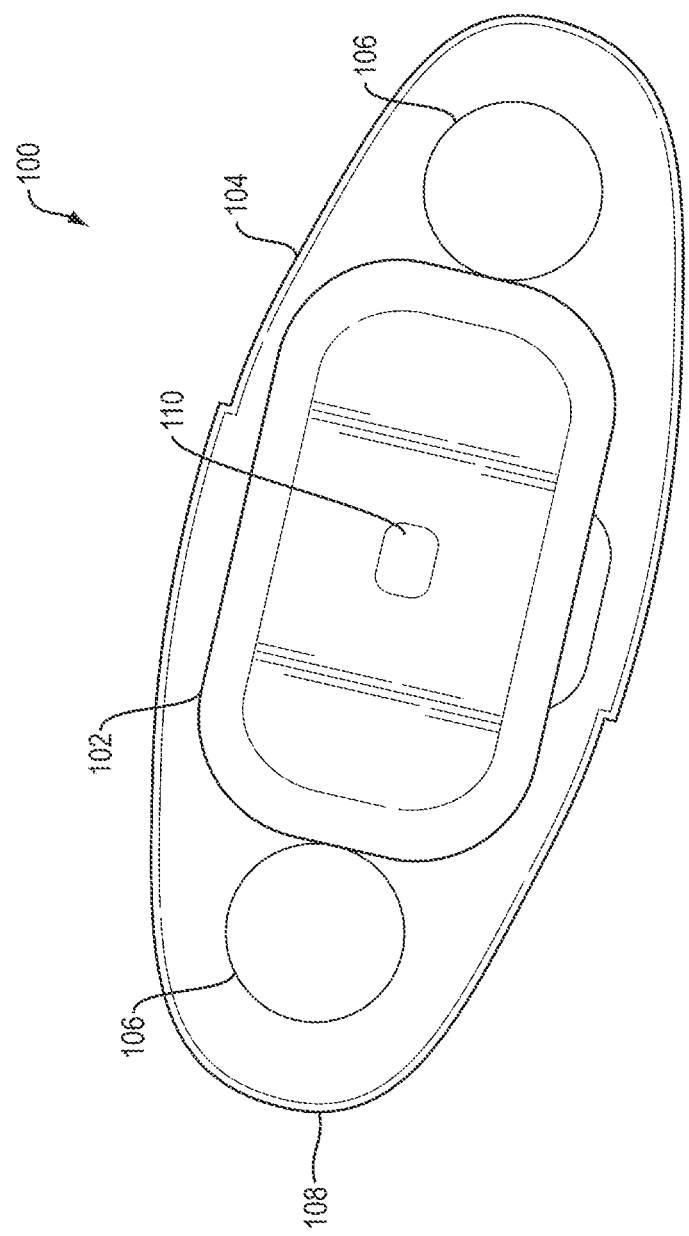
FIG. 1 is a top, elevation view of a wearable health monitor, configured in accordance with embodiments of the present disclosure.

Now referring to FIG. 1, a top, elevation view of a wearable health monitor 100, configured in accordance with embodiments of the present disclosure, is shown. The wearable health monitor 100 includes a housing 102 containing circuitry necessary to the operation of the sensor. The wearable health monitor 100 further comprises a mounting strip 104, in embodiments similar in size and shape to a medium sized adhesive bandage, onto which the housing 102 can be affixed. The mounting strip 104 is used to attach the housing 102 to a user and, in embodiments, comprises an adhesive layer disposed opposite the housing 102 such that the mounting strip 104 may be removably attached to a user in any convenient location.

In embodiments, the mounting strip comprises electrodes 106 in operative communication with the housing 102, when affixed to the mounting strip 104, allowing circuitry contained therein to use the electrodes to monitor biometric data of a user therethrough.

In embodiments, the mounting strip 104 comprises a release liner 108 disposed on the adhesive portion(s) thereof, to ensure the adhesive is not contaminated prior to use.

In embodiments, the housing 102 is reusable and contains a power supply. The power supply, in embodiments, is a rechargeable battery that may be recharged using inductive charging technology, a charging port, or other charging technologies, as would be known to one of ordinary skill in the art. In other embodiments, an internal disposable battery is user-replaceable. In still other embodiments, a capacitor is used as a power source, enabling rapid charging.

In embodiments, the housing 102 comprises a function button 110, which can be programmed to perform a variety of functions, as necessary or desired.

Figure 2A:
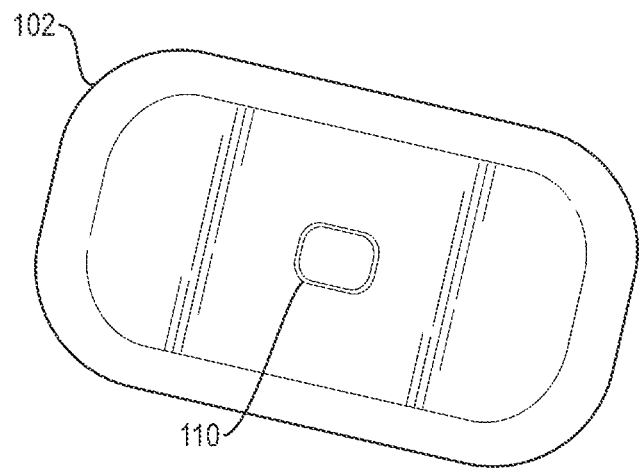
FIG. 2A is a top, elevation view of the circuitry-containing portion of a wearable health monitor, in accordance with embodiments of the present disclosure.

Now referring to FIG. 2A, a top, elevation view of the circuitry-containing portion of a wearable health monitor 100, the housing 102, in accordance with embodiments of the present disclosure, is shown.

Figure 2B:
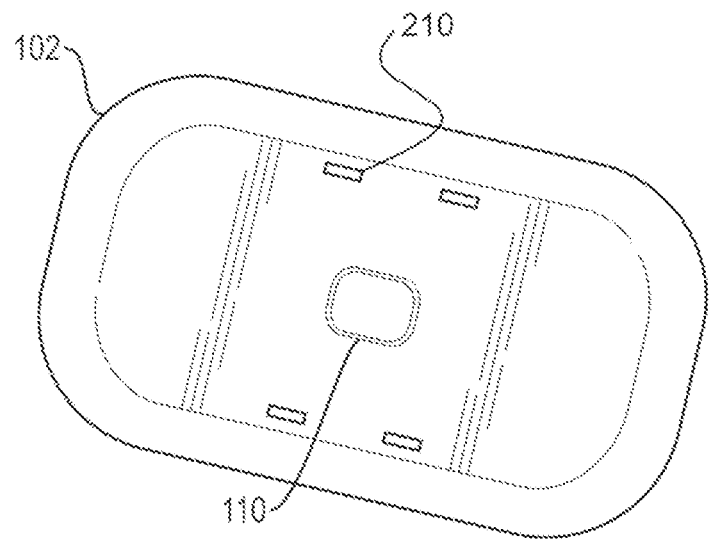
FIG. 2B is a top, elevation view of the circuitry-containing portion of a disposable wearable health monitor, in accordance with embodiments of the present disclosure.

In disposable embodiments, where the housing 102 is configured for at least semi-permanent attachment to the spine 200, such as that shown in FIG. 2B, the housing 102 comprises apertures configured to allow a special tool to be used to remove the housing 102 from the mounting strip 104. In embodiments, the housing 102 utilizes snap assemblies 202 featuring an undercut, such as those shown in FIG. 2E, or similar features, as would be known to one of ordinary skill in the art, to secure the housing 102 to the spine 200.

Figure 2C:
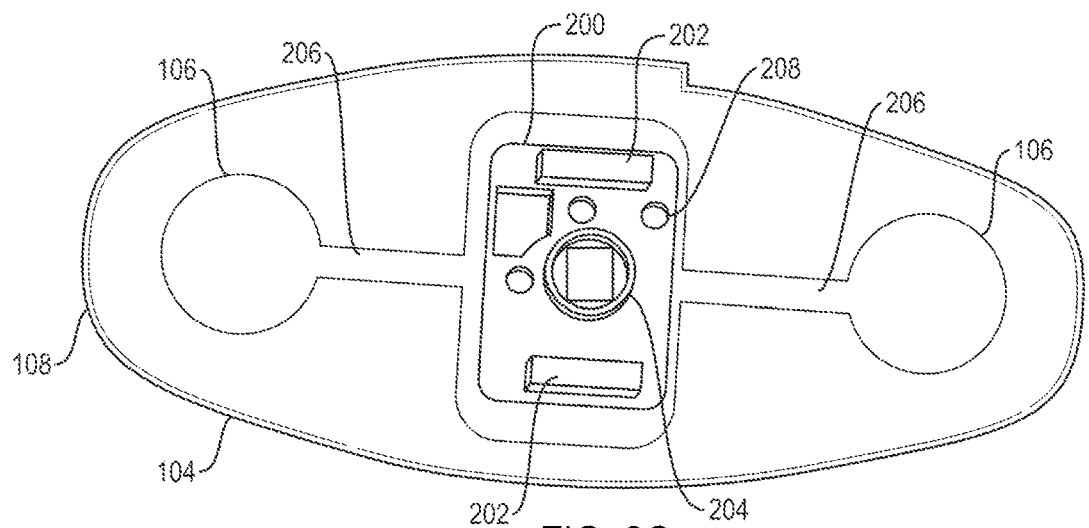
FIG. 2C is a top, elevation view of the adhesive portion of a wearable health monitor, in accordance with embodiments of the present disclosure.

FIG. 2C shows a top, elevation view of a mounting strip 104, in accordance with embodiments of the present disclosure, wherein the housing 102 has been removed therefrom. From this figure, it can be seen that the mounting strip comprises a relatively narrow spine 200 that is disposed substantially centrally on the mounting strip 104. Furthermore, the spine 200 comprises a connector 204 disposed substantially centrally thereon. The connector 204 is configured to provide electrical connectivity between the housing 102 and mounting strip 104, which, in embodiments, contains a variety of sensors (e.g. electrodes 106) and/or pass-throughs for sensors contained within the housing 102.

For example, in embodiments, apertures 208 in the spine 200 of mounting strip 104 align with Light Emitting Diodes (LEDs) disposed on the bottom of the housing 102, allowing for the measurement of oxygen saturation in a user. In embodiments, three apertures 208 are used to enable three different light frequencies to calculate blood oxygen saturation measurement.

In embodiments, fiber optic wires, fiber optic cables, light pipes, and/or similar light-conveying means are disposed in the mounting strip 104 and positioned to align with light-emitting elements in the housing 102. Many additional sensor types could be used in conjunction with the wearable health monitor 100 described herein, as would be known to one of ordinary skill in the art.

The spine 200 is, in embodiments, connected to electrodes through flexible connections 206, which may be wires, traces, or other types of flexible connections, as would be known to one of ordinary skill in the art.

In embodiments, the mounting strip 104 utilizes coupling features 202, in embodiments magnets, to secure the housing 102 thereto, utilizing corresponding magnetic materials disposed in the housing 102. In embodiments, these magnets 202 are phased magnets 202 that act to repel the housing 102 from the mounting strip 104 if the orientation of the two is incorrect (i.e. 180° off), discouraging users from assembling the components incorrectly. In embodiments, the magnets 202 are colored, with those colors corresponding to coloring disposed on the mounting strip 104, thereby providing a visual cue as to the correct orientation.

Figure 2D:
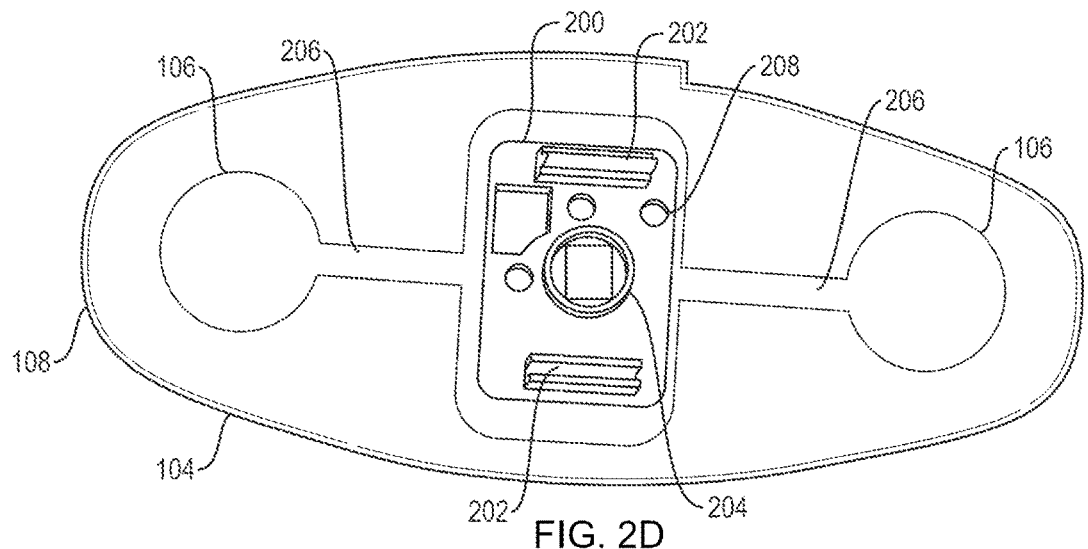
FIG. 2D is a top, elevation view of the adhesive portion of a wearable health monitor, in accordance with embodiments of the present disclosure.

In other embodiments, such as that shown in FIG. 2D, the coupling features 202 comprise one magnet having a female feature configured to mate with a corresponding magnet having a male feature disposed in the housing 102 and one magnet having a male feature configured to mate with a corresponding magnet having a female feature disposed in the housing 102, thus preventing the housing 102 from being installed on the spine 200 in an incorrect orientation while providing a visual cue as to the correct orientation.

Figure 2E:
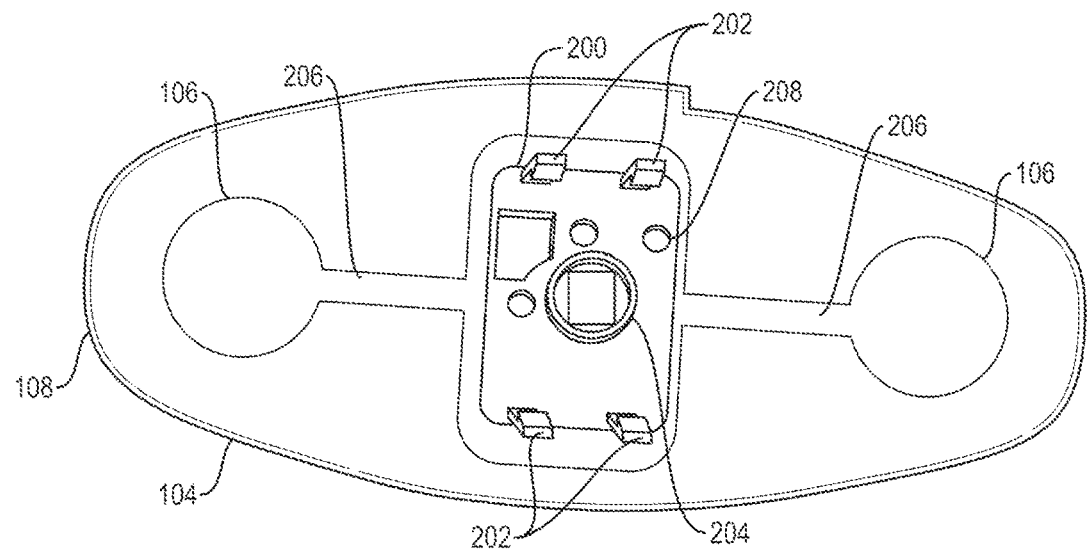
FIG. 2E is a top, elevation view of the adhesive portion of a disposable wearable health monitor, in accordance with embodiments of the present disclosure.

In other embodiments, such as that shown in FIG. 2E, the coupling features 202 comprise snap assemblies 202 disposed in the spine 200 and configured to mate with corresponding features disposed in the housing 102. While the snap assemblies disposed in the spine 200 are depicted as male features, these coupling features could be male, female, or a combination thereof without departing from the inventive concepts disclosed herein, as would be known to one of ordinary skill in the art.

In embodiments, the snap assemblies 202 are offset to prevent users from assembling the components incorrectly (i.e. 180° off). In embodiments, the snap assemblies 202 are alternating male and female assemblies to discourage users from assembling the components incorrectly.

In embodiments, a combination of coupling features 202, such as magnets and snap assemblies, is used to secure the housing 102 to the spine 200.

Figure 3:
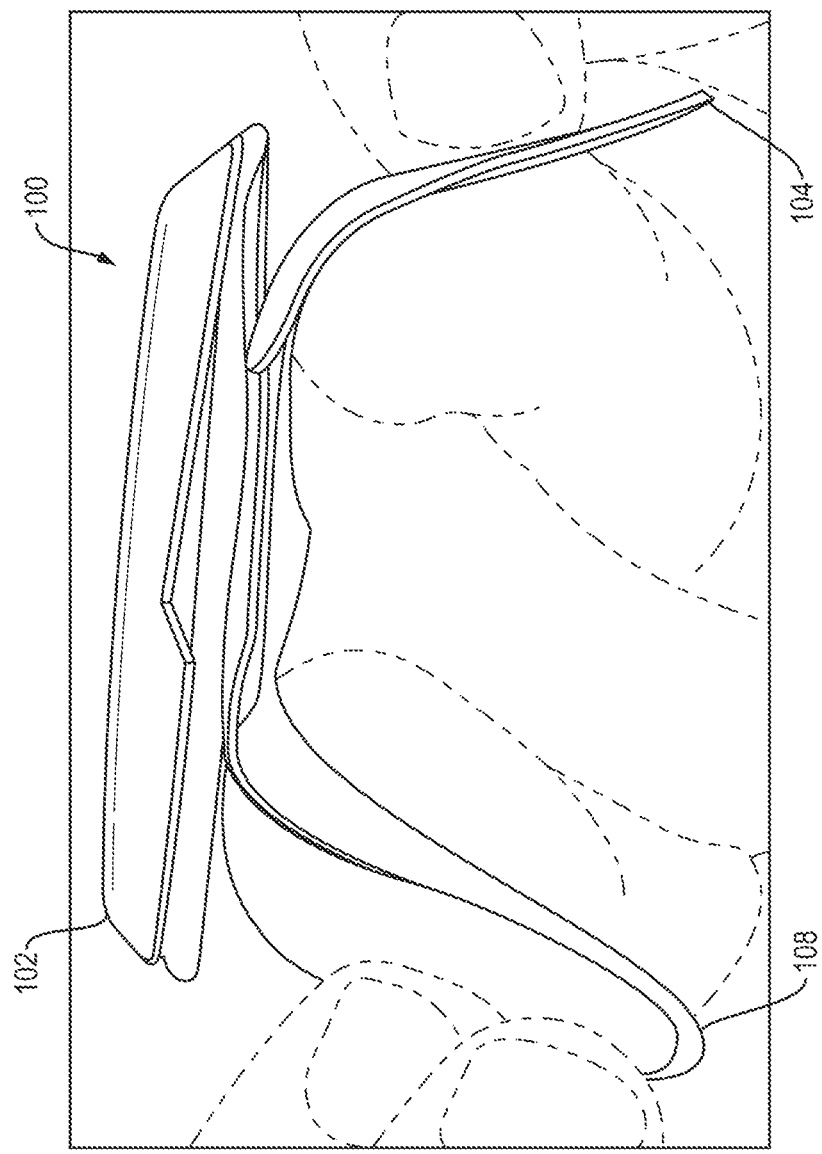
FIG. 3 is a side, elevation view of a wearable health monitor wherein the adhesive portion thereof is being flexed, in accordance with embodiments of the present disclosure.

Now referring to FIG. 3, the flexibility of the present invention is demonstrated through an illustration of the mounting strip 104 and release liner 108 in a highly flexed position, wherein the housing 102 is shown not to substantially limit the flexibility of the mounting strip 104, due to its attachment thereto only using the relatively narrow spine 200 thereof. By limiting the width of the area of attachment of the housing 102 to the mounting strip 104, the flexibility of the mounting strip 104 is vastly improved, enhancing both user comfort and the ability of the mounting strip 104 to remain attached to a user for long periods of time, since the mounting strip 104 is allowed to more freely contour itself to the user. Furthermore, the housing 102 can be made larger than previously feasible, since it does not need to lie flat against a user's body (i.e. the mounting strip 104 is free to contour itself to a user's body independently of the housing 102).

The modularity of the present invention further reduces the waste involved with prior art health sensors, by allowing the replacement of mounting strips 104 that no longer retain the housing 102 to a user adequately while allowing the more expensive and environmentally harmful circuitry and power sources, which are contained within the housing 102 to be reused.

Embodiments further allow for a housing 102 to be mounted on a variety of mounting strips 104, each of which may contain different sensors and/or pass-throughs, thereby reducing their cost, compared to a mounting strip 104 that provides measurement capabilities that are not needed in a given situation.

The modular wearable health monitor 100 of embodiments described herein also allows a user to easily remove the housing 102 when required, allowing them to engage in activities that may have been prevented when using prior art systems (e.g. a non-waterproof housing could be removed prior to showering or swimming, whereas prior art systems that are not removable from adhesive mounts might have to be covered or be made waterproof, resulting in additional expense and inconvenience).

Figure 4:
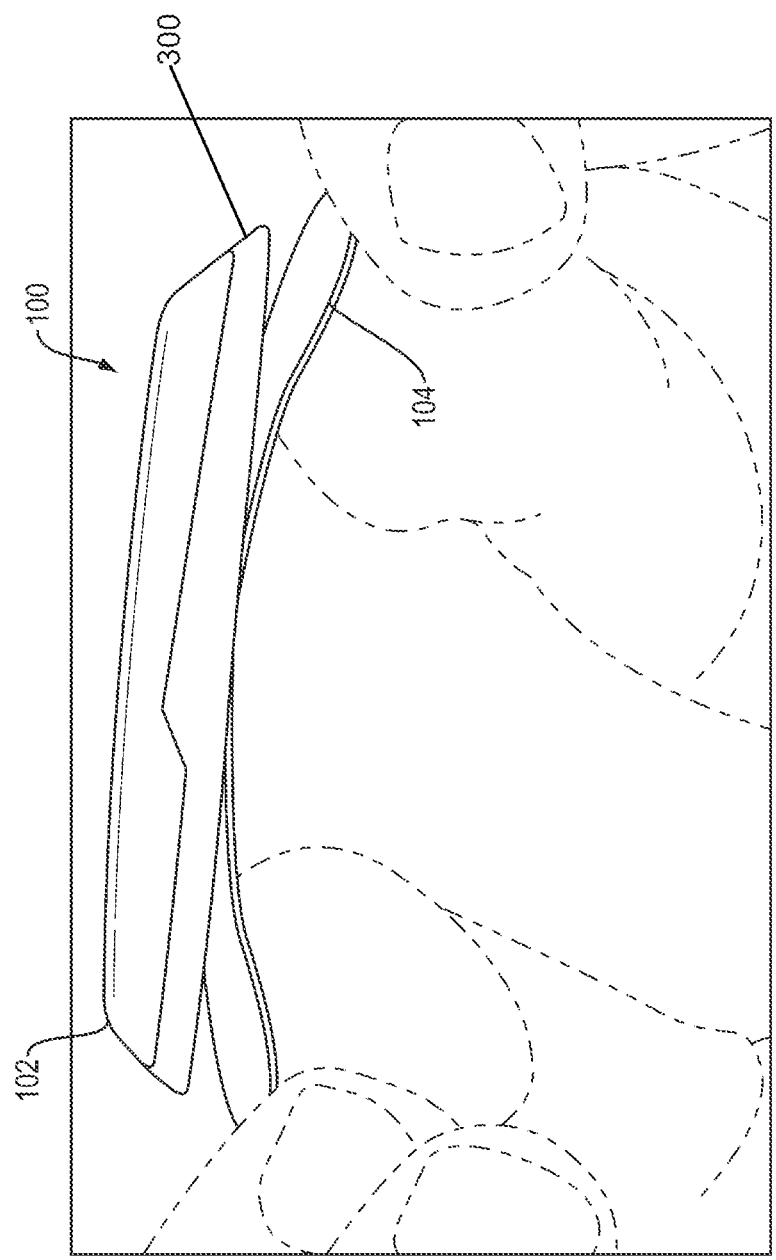
FIG. 4 is a side, elevation view of a wearable health monitor including a skirt configured to prevent clothing items and accessories from becoming trapped between the wearable health monitor and the body of a user, wherein the adhesive portion thereof is being flexed, in accordance with embodiments of the present disclosure.

Now referring to FIG. 4, FIG. 4 provides a side, elevation view of a wearable health monitor 100 including a skirt 300 configured to prevent objects, such as clothing items and accessories, from becoming trapped between the housing 102 and mounting strip 104 of the modular wearable health monitor 100 and/or between the wearable health monitor 100 and the body of a user.

In embodiments, the skirt 300 attaches to the housing 102. The skirt 300 is attached to the housing 102 using an adhesive or other form of bonding, through an over-molding operation, or using an interference fit, in various embodiments, with interference fit embodiments having the benefit that the skirt 300 is removable for cleaning. The foregoing methods of attaching the skirt 300 to the housing 102 are intended to be exemplary and non-limiting, as many other suitable methods of attachment would be known to one of ordinary skill in the art.

In other embodiments, the skirt 300 attaches to the mounting strip 104.

In embodiments, the skirt 300 is made of a compliant polymer, such as silicone, to allow it to conform to a body of a user and to the mounting strip 104 when the housing 102 is attached thereto.

Notwithstanding the foregoing, it would be apparent to a person of ordinary skill in the art that other ways of attaching the skirt 300 to the modular wearable health monitor 100 are certainly possible; the embodiments listed above are intended to be exemplary and non-limiting.

The foregoing description of the embodiments of the invention has been presented for the purposes of illustration and description. Each and every page of this submission, and all contents thereon, however characterized, identified, or numbered, is considered a substantive part of this application for all purposes, irrespective of form or placement within the application. This specification is not intended to be exhaustive or to limit the invention to the precise form disclosed. Many modifications and variations are possible in light of this disclosure.

What is claimed is:

1. A modular wearable health monitor comprising:
   a housing comprising a power source, at least one processor configured to process biometric data, and at least one housing coupling feature;
   a skirt disposed on the housing;
   a flexible mount configured, during use, to be affixed to a user's body, the flexible mount comprising an adhesive portion configured for adhering said flexible mount to the user's body; and
   a substantially rigid spine disposed substantially centrally on said flexible mount, the spine comprising at least one spine coupling feature configured to allow the spine to be connected to the housing via the at least one housing coupling feature disposed in the housing,
   wherein said spine is substantially narrower than said mount,
   wherein said housing is substantially wider than said substantially rigid spine,
   wherein the skirt is configured to extend down from the housing to the user's body during use, forming a cavity between the housing and the user's body that envelops at least a portion of the flexible mount,
   wherein outer edges of the housing are configured to lift away from the flexible mount as the user's body flexes,
   wherein the skirt is configured to remain in contact with the user's body and/or the flexible mount over a limited range of flex, and
   wherein said housing and substantially rigid spine are restrained from movement relative to one another once attached.

2. The modular wearable health monitor of claim 1 wherein said mount further comprises at least one sensor that, upon fixation of the housing to the spine, is put into electrical and/or optical communication with said housing.

3. The modular wearable health monitor of claim 1 wherein said spine further comprises apertures aligned with features of said housing.

4. The modular wearable health monitor of claim 3 wherein the features of said housing comprise Light Emitting Diodes.

5. The modular wearable health monitor of claim 1 wherein said at least one housing coupling feature and said at least one spine coupling feature comprise magnets.

6. The modular wearable health monitor of claim 5 wherein said magnets are phased magnets configured to repel the housing from the spine if the orientation of the two is incorrect.

7. The modular wearable health monitor of claim 1 wherein said at least one housing coupling feature and said at least one spine coupling feature comprise corresponding snap-fit features.

8. The modular wearable health monitor of claim 7 wherein said corresponding snap-fit features are configured to render the housing permanently affixed to the spine.

9. The modular wearable health monitor of claim 8 wherein the housing comprises apertures aligned with each of the at least one snap fit feature.

10. The modular wearable health monitor of claim 9 wherein the apertures are configured to allow the corresponding snap fit features to be disconnected through the use of a tool configured to be inserted therethrough.

11. The modular wearable health sensor of claim 1 wherein said skirt is attached to said housing using a technique selected from the group consisting of adhesive, over-molding, bonding, and interference fit.

12. The modular wearable health sensor of claim 1 wherein the at least one housing coupling feature comprises at least two housing coupling features, wherein the at least one spine coupling feature comprises at least two spine coupling features, and wherein the at least two housing coupling features and at least two spine coupling features are configured to provide a visual cue as to the correct orientation of the spine to the housing.

13. The modular wearable health sensor of claim 12 wherein the visual cue comprises color matching of corresponding housing coupling features and spine coupling features.

14. The modular wearable health sensor of claim 1 wherein the at least one housing coupling feature comprises at least two housing coupling features, wherein the at least one spine coupling feature comprises at least two spine coupling features, and wherein the at least two housing coupling features and at least two spine coupling features are configured to allow the spine to be connected to the housing only in a specific orientation.

15. The modular wearable health sensor of claim 14 wherein the at least two spine coupling features comprise one spine coupling feature having a male feature and one spine coupling feature having a female feature, wherein the at least two housing coupling features comprise one housing coupling feature having a male feature and one housing coupling feature having a female feature, and wherein the male features of one of the housing or spine are configured to be secured to the female feature of the other and vice-versa.

16. The modular wearable health sensor of claim 1 wherein the at least one housing coupling feature comprises at least two housing coupling features, wherein the at least one spine coupling feature comprises at least two spine coupling features, and wherein the at least two housing coupling features and at least two spine coupling features are disposed asymmetrically such that only a particular orientation of the housing to spine is possible.

17. A modular wearable health monitor comprising:
a flexible mount configured, during use, to be affixed to a user's body, the mount comprising a body attachment means for affixing said mount to the user's body;
a substantially rigid spine disposed substantially centrally on said flexible mount, the spine comprising an attachment means; and
a housing comprising a power source and at least one processor configured to process biometric data and further comprising a corresponding attachment means configured to allow the housing to be secured to the attachment means of the spine; and
a skirt disposed on the housing;
wherein said spine is substantially narrower than the mount,
wherein the skirt is configured to extend down from the housing to the user's body during use, forming a cavity between the housing and the user's body that envelops at least a portion of the flexible mount,
wherein outer edges of the housing are configured to lift away from the flexible mount as the user's body flexes,
wherein the skirt is configured to remain in contact with the user's body and/or the flexible mount over a limited range of flex, and
wherein said housing and substantially rigid spine are restrained from movement relative to one another once attached.

18. The modular wearable health sensor of claim 17 wherein said skirt is made of a compliant polymer.

19. A modular wearable health monitor comprising:
a housing comprising a power source, at least one processor configured to process biometric data, at least one housing coupling feature, and an aperture aligned with each at least one housing coupling feature;
a skirt disposed on the housing;
a flexible mount configured, during use, to be affixed to a user's body, the flexible mount comprising an adhesive portion configured for adhering said flexible mount to the user's body;
a substantially rigid spine disposed substantially centrally on said flexible mount, the spine comprising at least one spine coupling feature configured to allow the spine to be connected to the housing via the at least one housing coupling feature disposed in the housing; and
wherein said spine is substantially narrower than the mount,
wherein said housing is substantially wider than said spine,
wherein the skirt is configured to extend down from the housing to the user's body during use, forming a cavity between the housing and the user's body that envelops at least a portion of the flexible mount,
wherein outer edges of the housing are configured to lift away from the flexible mount as the user's body flexes,
wherein the skirt is configured to remain in contact with the user's body and/or the flexible mount over a limited range of flex,
wherein said at least one housing coupling feature and said at least one spine coupling feature comprise corresponding snap-fit features,
wherein said corresponding snap-fit features are configured to render the housing permanently affixed to the spine, and
wherein the apertures are configured to allow corresponding snap fit features to be disconnected through the use of a tool.

20. The modular wearable health monitor of claim 1 wherein the skirt is in contact with and attached to said housing only along a bottom, peripheral edge thereof.

* * * * *